United States Patent [19]

Reinhardt et al.

[11] 4,263,461

[45] Apr. 21, 1981

[54] POLYPHENYL ETHER COMPOUNDS

[75] Inventors: Bruce A. Reinhardt, New Carlisle; Fred E. Arnold, Centerville, both of Ohio

[73] Assignee: The United States of America as represented by the Secretary of the Air Force, Washington, D.C.

[21] Appl. No.: 88,505

[22] Filed: Oct. 26, 1979

[51] Int. Cl.³ .................. C07C 43/275; C07C 43/285
[52] U.S. Cl. .................................. 568/636; 544/353; 544/354; 252/188.3 R
[58] Field of Search ........................................ 568/636

[56] References Cited

U.S. PATENT DOCUMENTS 3,756,982   9/1973   Korshak et al. ................ 568/636 X

*Primary Examiner*—Bernard Helfin
*Attorney, Agent, or Firm*—Donald J. Singer; William J. O'Brien

[57] ABSTRACT

Acetylene-substituted aromatic ethers having very low glass transition temperatures. The compounds are useful as reactive diluents for high Tg, acetylene-terminated phenylquinoxaline oligomers. When mixed with the oligomers, the resulting compositions have a lowered Tg and the necessary flow for melt processing.

3 Claims, No Drawings

POLYPHENYL ETHER COMPOUNDS

RIGHT OF THE GOVERNMENT

The invention described herein may be manufactured and used by or for the Government of the United States for all governmental purposes without the payment of any royalty.

FIELD OF THE INVENTION

This invention relates to reactive diluents for high temperature thermoset resins. In one aspect it relates to a process for preparing the reactive diluents.

BACKGROUND OF THE INVENTION

In advanced aircraft and aerospace systems, there is a need for high temperature thermoset resins for matrix and adhesive applications. Such resins, because of the complexity of structure, high glass transition temperature needed and high temperature thermooxidative stability required, have critical processing difficulties when required to conform to the state-of-the-art processing criteria. OSHA requirements negate processing such materials from solvent base systems, thereby necessitating fabrication of the resins via melt techniques.

As disclosed in U.S. Pat. Nos. 3,966,729 and 4,147,868, recent advances in matrix and adhesive resins have resulted from the discovery of a family of new phenylquinoxaline resins terminated by primary acetylene groups. The acetylene moiety can be thermally homopolymerized between 200° and 250° C. to form a moisture insensitive, high temperature resin system. Although the materials show excellent resistance to heat and environmental surroundings, the oligomers lack the necessary flow for melt processing because of their high glass transition temperatures (Tg = 140°–170° C.).

It is a principal object of this invention, therefore, to provide reactive diluents which, when mixed with certain selected phenylquinoxaline oligomers, provide compositions having good flow characteristics.

Another object of the invention is to provide reactive diluents which are completely compatible with certain selected phenylquinoxaline oligomers.

A further object of the invention is to provide reactive diluents which on thermal treatment co-cure with certain selected phenylquinoxaline oligomers.

Other objects and advantages of the invention will become apparent to those skilled in the art upon consideration of the accompanying disclsoure.

SUMMARY OF THE INVENTION

The present invention resides in acetylene-substituted aromatic compounds having the following structural formulas:

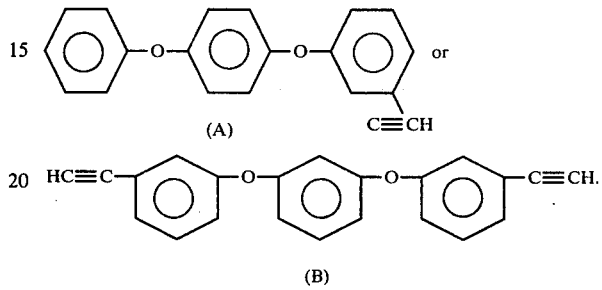

The compounds are structurally designed to exhibit very low glass transition temperatures (A = −49° C.; B = −39° C.). When mixed with high Tg, acetylene-terminated phenylquinoxaline oligomers, the compounds function as reactive diluents, effectively lowering their Tg for adequate flow for melt processing.

In one embodiment, the present invention is concerned with a process for preparing the acetylene-containing reactive diluent by a two-step reaction sequence. The reactions involved can be represented by the following equations:

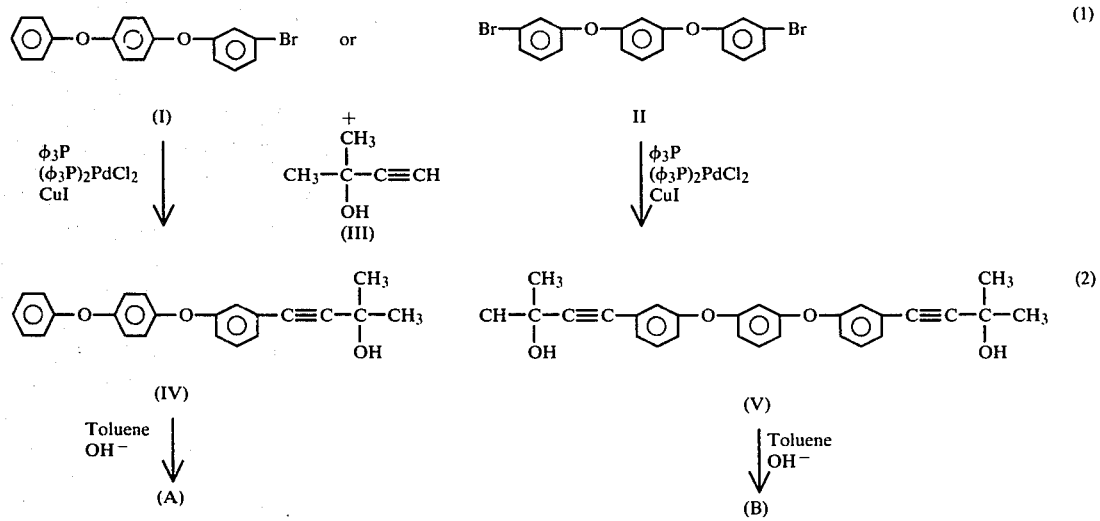

As shown by equation (1), in the first step of the process, mono or bisbromoaromatic ethers (I or II) are reacted with 2-methyl-3-butyne-2ol (III) in the presence of a catalytic amount of bistriphenylphosphine palladium II dichloride, cuprous iodide and triphenylphosphine. The reaction is carried out in triethylamine in an inert atmosphere under reflux conditions for a period of about 18 to 36 hours. In this reaction the bromine atoms of compounds I or II are displaced with a methylbutynol group to provide intermediates IV or V.

According to equation (2), intermediates IV or V are converted to acetylene-containing compounds, A or B. Conversion of the intermediates to primary acetylenes is carried out by the hydrolytic displacement of acetone with potassium hydroxide in toluene. The reaction is conducted in an inert atmosphere under reflux condition for a period of about 1 to 4 hours.

The acetylene-substituted reactive diluents are completely compatible with the family of high Tg, acetylene-terminated phenylquinoxaline oligomers disclosed in U.S. Pat. No. 4,147,868 which issued to one of us as a coinventor on Apr. 3, 1979. The disclosure of this patent is incorporated herein by reference. When mixed with the oligomers, the reactive diluents effectively lower their Tg to provide compositions having adequate flow for melt processing. Further details regarding the compositions are disclosed in our copending patent applications Ser. No. 88,504 filed on Oct. 26, 1979, the disclosure of which is incorporated herein by reference. A more complete understanding of the invention can be obtained by referring to the following illustrative examples which are not intended, however, to be unduly limitative of the invention.

EXAMPLE I

1-Phenoxy-3-(m-ethynylphenoxy)benzene (A)

A solution of 24.6 g (0.726 mol) of 1-phenoxy-3-(m-bromophenoxy)benzene, 6.31 g (75.0 mmol) of 2-methyl-3-butyn-2ol) and 0.36 g triphenylphosphine in 200 ml triethylamine was degassed with nitrogen for 20 minutes. To the degassed solution was added 0.036 g (0.0508 mmol) of bis-triphenylphosphine palladium II dichloride and 0.14 g (0.755 mmol) cuprous iodide. The mixture was heated to reflux for 24 hours, cooled to room temperature and the triethylamine removed under reduced pressure. The resulting yellow-green oil was dissolved in methylene chloride, dried over MgSO$_4$, filtered and chromatographed on silica gel using 1:1 methylene chloride-hexane as the eluent. After the solvent was removed under reduced pressure, 24.0 g (96%) of an organe oil was recovered.

Analysis Calc'd for C$_{23}$H$_{19}$O$_3$: C,80.21; H, 5.56. Found: C,79.85; H,5.39.

A solution of 24.0 g (0.0697 mol) of the butynol adduct, a mixture of 0.75 g of potassium hydroxide dissolved in 20 ml of methanol, and 100 ml of toluene was heated to reflux under nitrogen. During the course of two hours the methanol and 60 ml of toluene were removed by distillation. The remaining toluene was removed under reduced pressure. The resulting dark oil was chromatographed on silica gel using 3:1 hexane-methylene chloride as the eluent. The solvent was removed under reduced pressure to give 17.10 g (81.7%) of a light yellow, viscous oil.

Analysis Calc'D for C$_{20}$H$_{13}$O$_2$: C,83.90; H,4.58. Found: C,83.30; H,4.62.

EXAMPLE II

1,3-Bis-(m-ethynylphenoxy)benzene (B)

A mixture of 12.60 g (0.03 mole) of 1,3-bis-(m-bromophenoxy)-benzene and 6.03 g (0.072 mole) of 2-methyl-3-butyn-3-ol and 100 ml of triethylamine was degassed by passing nitrogen through the solution for 20 minutes. To the reaction mixture was then added 0.03 g (0.042 mmol) of bis-triphenylphosphine palladium II dichloride, 0.12 g (0.624 mmol) of cuprous iodide and 0.30 g (1.14 mmol) of triphenylphosphine. The temperaure of the reaction mixture was raised to 80° C. and maintained there for 24 hours. The reaction was then cooled to room temperature, and the triethylamine was removed under reduced pressure. The resulting yellow-red oil was chromatographed on a 5 cm × 60 cm dry silica gel column (quartz) using 1:1 hexane-ether as the eluent. The second fluorescent band was collected (appears yellow on the column). The solvent was removed under reduced pressure to yield 10.6 g (83%) of a dark viscous oil. The product was used in the next step of the reaction sequence without further purification.

A mixture of 10.6 g of the bis-butynol adduct and 0.75 g of KOH in 20 ml of anhydrous methanol were added to 100 ml of toluene and heated to reflux under nitrogen. The methanol and 40 ml of the toluene were then removed by distillation over a period of two hours. The reaction was monitored by TLC on silica gel plates containing fluorescent indicator using 3:1 hexane-methylene chloride as the developing solvent. The product appeared as the first spot to be eluted. The reaction was judged to be complete when no starting material appeared at the origin of the TLC plate after development. After a total reaction time of two hours, the reaction mixture was cooled, and the toluene removed at 35° C. under reduced pressure. The red viscous residue was chromatographed on a dry 5 cm × 60 cm column (quartz) of silica gel using 3:1 hexanemethylene chloride. The first large fluorescent band was collected and the solvent removed at 50° C. under high vacuum. The last traces of hexane were removed by pumping on the yellow oil for 18 hours at 0.2 mm pressure. The yield of pure product was 6.1 g (79%).

Analysis Calc'd for C$_{22}$H$_{14}$O$_2$: C,85.07; H,4,54. Found: C84.72; H,4.23.

EXAMPLE III

Samples of the reactive diluents prepared in Examples I and II were mixed with an acetylene-terminated phenylquinoxaline oligomer having the following formula:

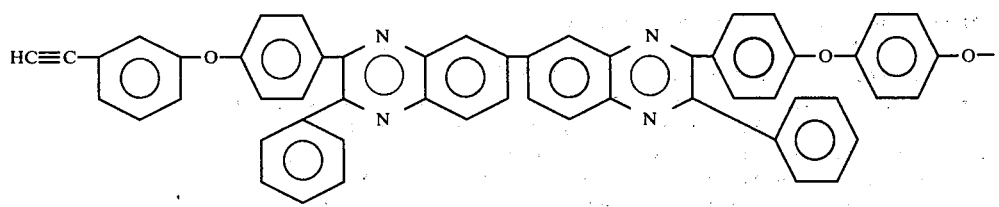

-continued

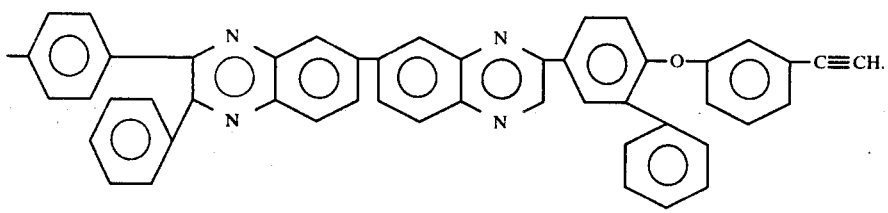

The oligomer was prepared as described in U.S. Pat. No. 4,147,868.

Mixing of the materials was accomplished by dissolving various amounts of the reactive diluents and oligomer in methylene chloride after which the solvent was removed under reduced pressure. Small samples of the various mixtures were placed in test tubes. The tubes were heated at 280° C. for 6 hours, removed and allowed to cool to room temperature. Thermal mechanical analysis (TMA) or differential scanning calorimetry (DSC) was determined on the non-cured and co-cured mixtures to determine the reduction in Tg or the effective lowering of Tg for fabrication. The data obtained are shown below in the table.

TABLE

| % Diluent | % Oligomer | Tg °C.[1] Uncured | Tg °C.[2] Co-cured[4] | Reduction[3] Tg °C. |
|---|---|---|---|---|
| 100 (A) | 0 | −49° C. | | |
| 100 (B) | 0 | −39° C. | | |
| 0 | 100 | 165° C. | | |
| 20 (A) | 80 | 91° C. | 223° C. | 74° C. |
| 30 (A) | 70 | 70° C. | 184° C. | 95° C. |
| 10 (B) | 90 | 106° C. | 311° C. | 59° C. |
| 20 (B) | 80 | 72° C. | 306° C. | 93° C. |
| 30 (B) | 70 | 58° C. | 314° C. | 107° C. |

[1]Determined by DSC at a heating rate of 20° C./min.
[2]Determined by TMA at a heating rate of 20° C./min.
[3]Reduction in Tg of oligomer resulting from reactive diluent
[4]Mixture co-cured at 280° C. for 6 hours.

As seen from the foregoing, the present invention provides acetylene-substituted aromatic ethers which function as reactive diluents for high Tg acetylene-terminated phenylquinoxaline oligomers. Thus, when the reactive diluents are mixed with the oligomers, the resulting compositions have a reduced Tg and thereby acquire the necessary flow characteristics for melt processing.

As will be apparent to those skilled in the art, modifications of the present invention can be made in view of the foregoing disclosure without departing from the spirit and scope of the invention.

We claim:

1. A compound selected from the group of compounds having the following structural formulas:

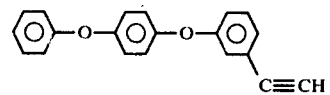

and

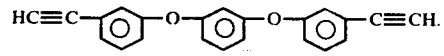

2. The compound according to claim 1 having the following structural formula:

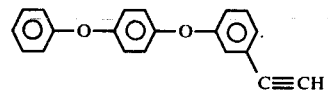

3. The compound according to claim 1 having the following structural formula:

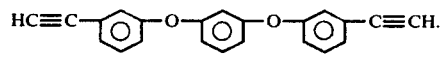

* * * * *